United States Patent
Kärki

(10) Patent No.: US 10,317,340 B2
(45) Date of Patent: Jun. 11, 2019

(54) APPARATUS AND METHOD FOR OPTICALLY MEASURING FLUIDAL MATTER HAVING FLUID AS MEDIUM AND PARTICLES NON-DISSOLVED IN MEDIUM

(71) Applicant: VALMET AUTOMATION OY, Espoo (FI)

(72) Inventor: Pasi Kärki, Kajaani (FI)

(73) Assignee: VALMET AUTOMATION OY, Espoo (FI)

( * ) Notice: Subject to any disclaimer, the term of this patent is extended or adjusted under 35 U.S.C. 154(b) by 0 days.

(21) Appl. No.: 15/836,277

(22) Filed: Dec. 8, 2017

(65) Prior Publication Data

US 2018/0172585 A1     Jun. 21, 2018

(30) Foreign Application Priority Data

Dec. 19, 2016 (FI) ...................................... 20165988

(51) Int. Cl.
| | |
|---|---|
| *G01N 21/53* | (2006.01) |
| *G01N 21/49* | (2006.01) |
| *G01N 15/00* | (2006.01) |
| *G01N 33/34* | (2006.01) |
| *G01N 21/51* | (2006.01) |
| *G01N 21/47* | (2006.01) |

(52) U.S. Cl.
CPC ........... *G01N 21/534* (2013.01); *G01N 15/00* (2013.01); *G01N 21/49* (2013.01); *G01N 21/51* (2013.01); *G01N 33/343* (2013.01); *G01N 2021/4769* (2013.01)

(58) Field of Classification Search
CPC ...... G01N 21/49; G01N 21/534; G01N 15/00; G01N 2021/4769; G01N 21/51; G01N 33/343
USPC .................................................. 356/432–444
See application file for complete search history.

(56) References Cited

U.S. PATENT DOCUMENTS

| | | | |
|---|---|---|---|
| 5,420,682 A | 5/1995 | Haggerty et al. | |
| 5,497,232 A | 3/1996 | Watano et al. | |
| 5,992,245 A | 11/1999 | Takei et al. | |
| 2005/0246762 A1 | 11/2005 | Girouard et al. | |

FOREIGN PATENT DOCUMENTS

WO    01/53810 A1    7/2001

OTHER PUBLICATIONS

Jun. 8, 2017 Search Report issued in Finland Patent Application No. 20165988.
Pougatch, Konstantin et al., "Simulation of particle attrition by supersonic gas jets in fluidized beds," Chemical Engineering Science vol. 65, 2010, pp. 4829-4843.
Sep. 21, 2018 Search Report issued in Swedish Patent Application No. 1751527-1.

*Primary Examiner* — Tri T Ton
(74) *Attorney, Agent, or Firm* — Oliff PLC

(57) ABSTRACT

An apparatus for optically measuring fluidal matter having fluid as medium and particles non-dissolved in the medium wherein the apparatus comprises a measurement chamber, which is configured to contain the fluidal matter, and a nozzle. The nozzle receives flowable matter and emits a jet of the flowable matter towards or fromwards an optical detector which is associated with the measurement chamber and receives optical radiation from the fluidal matter in the measurement chamber.

11 Claims, 4 Drawing Sheets

APPARATUS AND METHOD FOR OPTICALLY MEASURING FLUIDAL MATTER HAVING FLUID AS MEDIUM AND PARTICLES NON-DISSOLVED IN MEDIUM

FIELD

The invention relates to an apparatus and a method for optically measuring fluidal matter having fluid as medium and particles non-dissolved in the medium.

BACKGROUND

Because an optical power source cable is close to a detector cable in the kappa measurement, for example, the fibers of the suspension have to be separate. Flocks, which easily form, cause noise-like variation in the optical signal which deteriorates the reliability of the measurement results.

The problem has been mitigated by increasing a measurement period and averaging the results over the measurement period. This kind of integration over time makes the measurement very slow. Hence, there is a need to improve the measurements.

BRIEF DESCRIPTION

The present invention seeks to provide an improvement in the measurements. According to an aspect of the present invention, there is provided an apparatus as specified in claim 1.

According to another aspect of the present invention, there is provided a method in claim 11.

The invention has advantages. A jet of flowable matter breaks at least a part of aggregates in the fluidal matter in front of a detector, and homogenizes the measured part of the fluidal matter.

LIST OF DRAWINGS

Example embodiments of the present invention are described below, by way of example only, with reference to the accompanying drawings, in which FIG. 1A illustrates an example of an apparatus for optically measuring fluidal matter, a jet and reception of the optical radiation having the same direction;

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

It should be noted that while Figures illustrate various embodiments, they are simplified diagrams that only show some structures and/or functional entities. The connections shown in the Figures may refer to logical or physical connections. It is apparent to a person skilled in the art that the described apparatus may also comprise other functions and structures than those described in Figures and text. It should be appreciated that details of some functions, structures, and the signalling used for operation are irrelevant to the actual invention. Therefore, they need not be discussed in more detail here.

Figure 1A:
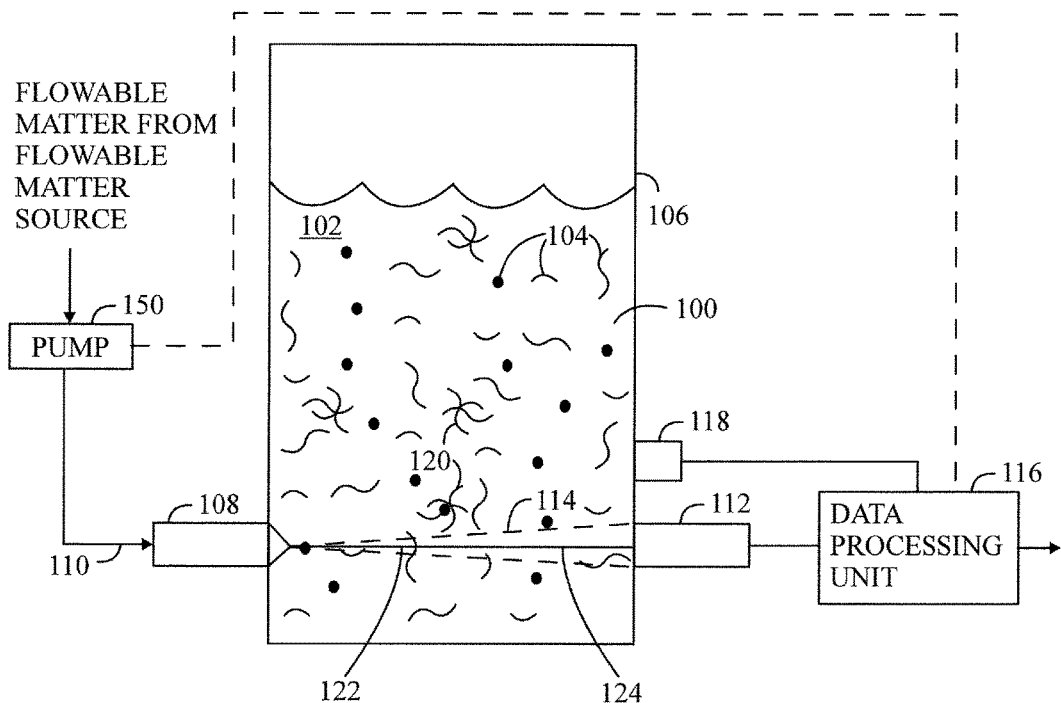
FIG. 1B illustrates an example of an apparatus for optically measuring fluidal matter, a jet and reception of the optical radiation having an opposite direction.
Figure 1B:
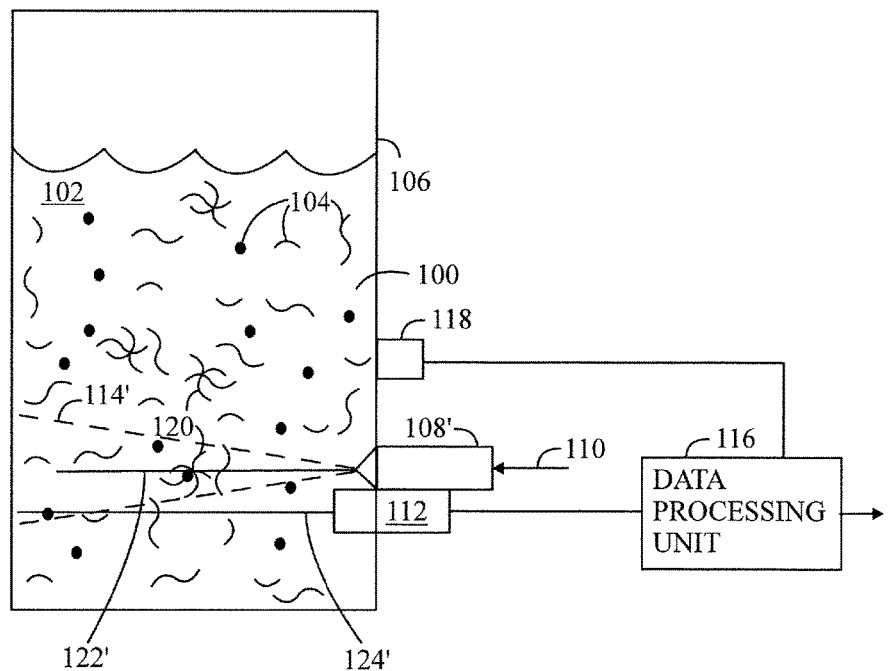

FIGS. 1A and 1B illustrate examples of an apparatus for optically measuring fluidal matter 100. The fluidal matter 100 has fluid as medium 102 and particles 104 non-dissolved in the medium 102. The fluid may be liquid or gas. In an embodiment, the particles 104 may be insoluble. In an embodiment, the particles 104 may not have dissolved in the medium 102 at the moment of the measurement but may dissolve within a longer period of time. The fluidal matter may be flowing matter which can easily be reshaped without changing its density. In an embodiment, the fluidal matter 100 may be suspension. The medium 102 of the suspension may be water. The suspension may be wet pulp slurry, sewage or water/liquid having mineral particles of mineral processing. The particles in pulp slurry may be wood fibers, fines and/or other solid particles of paper industry. In an embodiment, the medium 102 may be gas and the particles 104 may be combustion particles of smoke.

The apparatus comprises a measurement chamber 106, which contains the fluidal matter 100. In an embodiment, a sample of the fluidal matter 100 may be taken from a main process pipe to the measurement chamber 100. In an embodiment, no sample is taken and the main process pipe is the measurement chamber 100. The apparatus also comprises at least one nozzle 108, 108'.

The at least one nozzle 108, 108' receives flowable matter 110. In an embodiment, the flowable matter may be gas. In an embodiment, the flowable matter 110 may also be flowing matter which can easily be reshaped without changing its density. In an embodiment, the flowable matter 110 may be water or some other liquid. In an embodiment, the flowable matter 110 may not have solid particles. The at least one nozzle 108, 108' emits a jet 114, 114' of the flowable matter 110 towards or fromwards an optical detector 112.

In the example of FIG. 1A, the jet 114 flows towards the optical detector 112. The jet 114, 114' may become wider like a cone, which has an opening angle (a solid angle), as the distance from the nozzle 108, 108' becomes larger. The jet is directed towards the optical detector 112, if any part of the jet 114, 114' hits the optical detector 112. That is, the optical detector 112 may then be within the opening (solid) angle of the jet 114, 114'.

FIG. 1B, in turn, illustrates an example of an embodiment where the nozzle 108' emits the jet 114' away from the optical detector 112. In this embodiment, the nozzle 108, 108' may be in the vertex or adjacent to the vertex of the opening angle of the (cone-like) jet 114, 114'.

In an embodiment, the jet 114 is directed at the optical detector 112. In an embodiment, the jet 114' is directed outwards from the optical detector 112. The nozzle 108' which emits the jet 114' fromwards the optical detector 112 may be adjacent to the optical detector 112, and more particularly the nozzle 108' which emits the jet 114' fromwards the optical detector 112 may be directly adjacent to the optical detector 112. That is, the nozzle 108' may be in physical contact with the optical detector 112. Because of adjacency between the optical detector 112 and the nozzle 108', turbulence of the jet 114 mixes the fluidal matter 106 which is in front of the detector 112 and disturbs the particles 104 and keeps them moving separately.

The optical detector 112 is associated with the measurement chamber 106, which means that the optical detector 112 is in physical contact with the measurement chamber 106. The end of the optical detector 112 may be at the wall level or inside the measurement chamber 106. The optical detector 112 receives optical radiation from the fluidal matter 100 in the measurement chamber 106. The optical detector 112 outputs an electrical signal in response to the detected optical radiation.

In an embodiment, the apparatus may comprise the optical detector 112 or the optical detector 112 may be operationally connected with a processing unit 116. The processing unit 116 may comprise at least one processor and at least one memory. The memory may include a suitable computer program code for processing the electrical signal from the optical detector 112.

In an embodiment, the optical detector 112 may comprise a photosensor. In an embodiment, the optical detector 112 may comprise pigtailed photosensor. In an embodiment, the optical detector 112 may comprise a camera. In an embodiment, the optical detector 112 may comprise spectrometer for processing more than one band of the detected optical radiation separately.

In an embodiment, the apparatus may comprise an optical radiation source 118 for illuminating the fluidal matter 100 in the measurement chamber 106. The optical radiation source 118 may comprise a led, an incandescent lamp, a halogen lamp, a gas discharge lamp, any combination thereof or the like, for example.

In an embodiment, the jet 114 of the at least one nozzle 108, 108' may break aggregates 120 of the particles 104 at least temporarily for the measurement. The aggregates 120 may include flocculates or flocks of fibers.

Figure 2A:
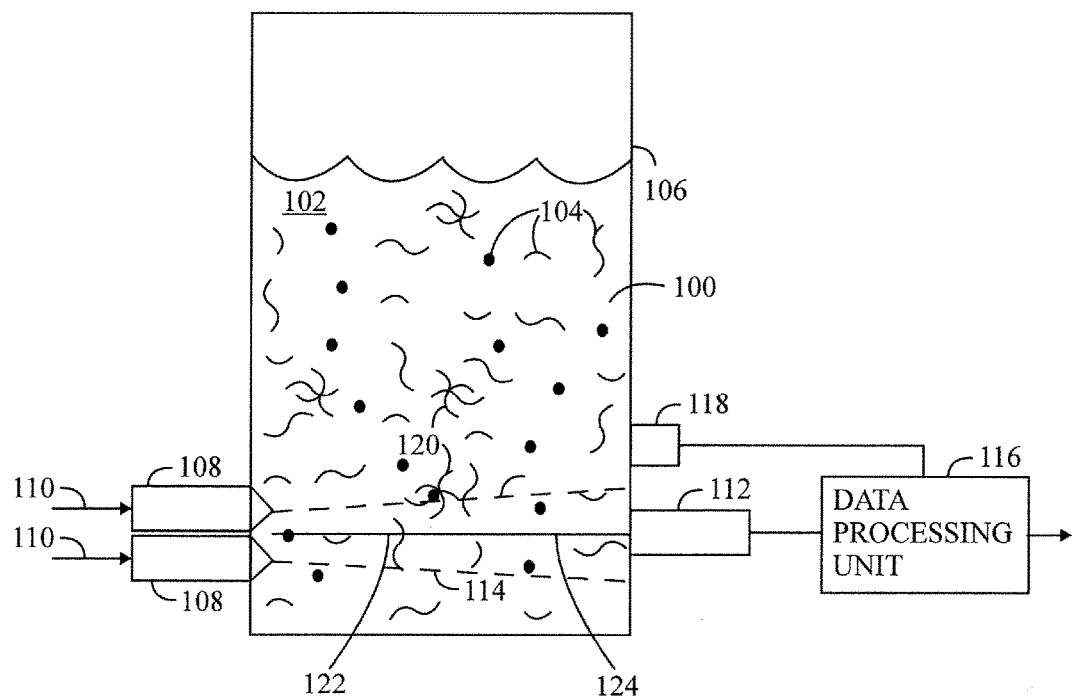
FIG. 2A illustrates an example of an apparatus for optically measuring fluidal matter, the apparatus having a plurality of nozzles opposite to detection.

FIG. 2A illustrates an example of an embodiment where there are at least two nozzles 108 emitting a combined jet 114 towards the optical detector 112. The longitudinal axis 122 of the combined jets 114 of the at least two nozzles 108 is parallel to the optical axis 124 in the example of FIG. 2B.

Figure 2B:
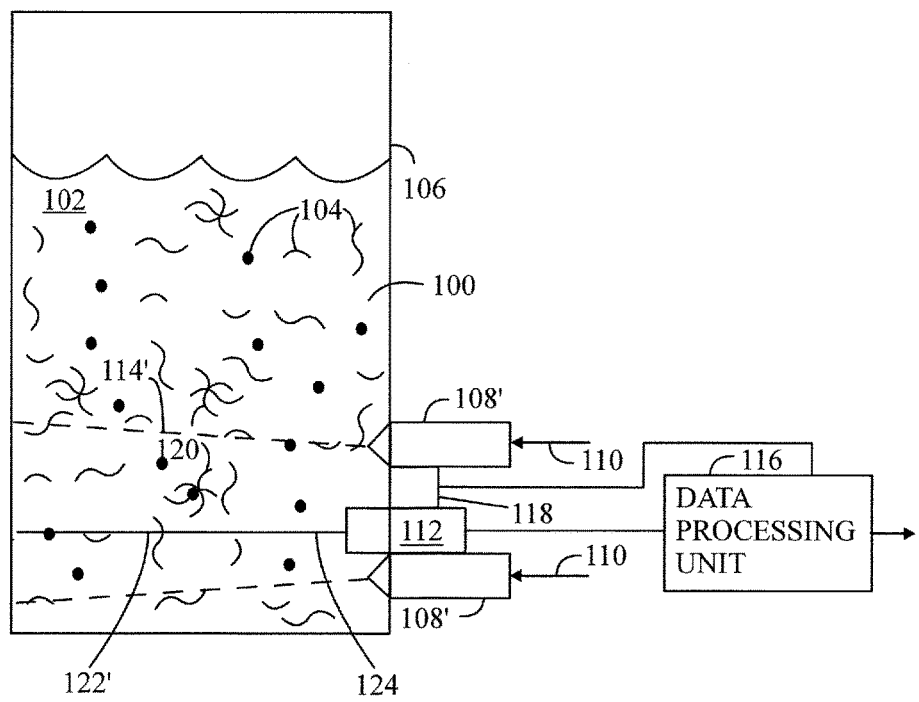
FIG. 2B illustrates an example of an apparatus for optically measuring fluidal matter, the apparatus having a plurality of nozzles on the same side with detection.

FIG. 2B illustrates an example of an embodiment where there are at least two nozzles 108' around the optical detector 112. The longitudinal axis 122' of the combined jet 114' of the at least two nozzles 108' is parallel to the optical axis 124 in the example of FIG. 2B. FIG. 2B illustrates an example where the optical detector 112 and the optical radiation source 118 may be combined. The combination may mean that the optical detector 112 and the optical radiation source 118 may be structurally integrated together. In an embodiment, the at least two nozzles 108', the optical detector 112 and the optical radiation source 118 may be structurally integrated together.

Figure 3:
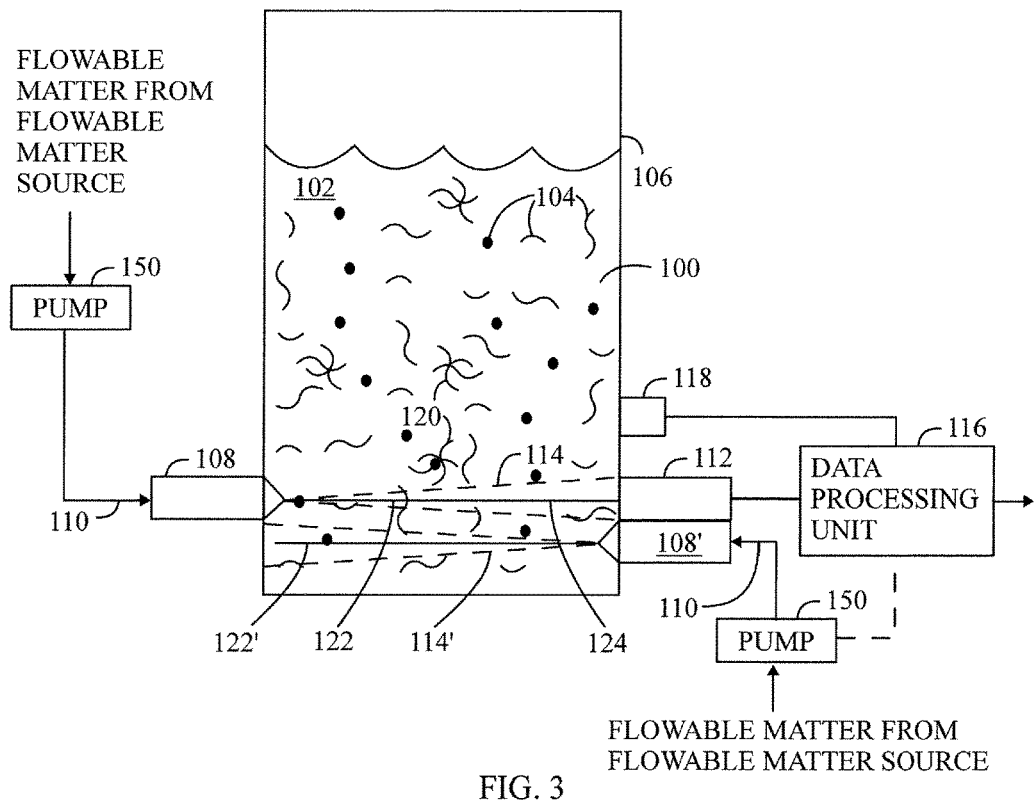
FIG. 3 illustrates an example of an apparatus for optically measuring fluidal matter, the apparatus having a plurality of nozzles on both the same and opposite side with detection.

FIG. 3 illustrates an example of an embodiment, where the apparatus has nozzles 108, 108' at opposite sides of the measurement chamber 106 in a manner which is similar to a combination of apparatuses of FIGS. 1A and 1B.

In an embodiment an example of which is shown in FIGS. 2A, 2B and 3, the apparatus may comprise at least two nozzles 108, 108'. The nozzles 108, 108', which emit their jets 114, 114', may reside in different locations in the measurement chamber 106. In an embodiment, the nozzles 108, 108' reside in opposite sides of the measurement chamber 106 for causing their flows of jets 114, 114' to have opposite directions.

The jet or jets 114, 114' in all embodiments may cause turbulence therearound while flowing through the fluidal matter 100. The turbulence disturbs and causes forces on the particles 104 and aggregates 120 adjacent to the jet or jets 114, 114'. As a result, not only the aggregates 120 directly hit by the jet or jets 114, 114' but also the aggregates 120 near the jet or jets 114, 114' will disintegrate into separate particles at least partly. The optical measurement gives more reliable results when measured from fluidal matter 100 having separate particles 104 than from fluidal matter 100 with aggregates 120.

In an embodiment, the nozzle 108 may emit its jet 114 of the flowable matter 110 such that the longitudinal axis 122 of each of the jet 114 and the optical axis 124 of the optical detector 112 are co-axial. If, in an embodiment, the nozzle 108', which is adjacent to the optical detector 112, has a circular mouth piece around the optical detector 112, it may also emit its jet 114' of the flowable matter 110 such that the longitudinal axis 122 of each of the jet 114' and the optical axis 124 of the optical detector 112 are co-axial. If, in an embodiment, the nozzle 108' is made of a plurality of sub-nozzles adjacently around the optical detector 112, the sub-nozzles may emit their combined jet 114' of the flowable matter 110 such that the longitudinal axis 122 of each of the jet 114' and the optical axis 124 of the optical detector 112 are co-axial.

In an embodiment, a direction of flow of a jet 114 from the nozzle 108 along the longitudinal axis 122 of the jet 108 is co-directional with the reception direction of the optical radiation. In an embodiment shown in FIG. 1A, the direction of the flow of a jet 114 from the nozzle 108 along the longitudinal axis 122 of the jet 108 is co-directional with the optical axis 124 of the optical detector 112.

In an embodiment, a direction of flow of a jet 114' from the nozzle 108' along the longitudinal axis 122 of the jet 114' may be opposite-directional to the reception direction of the optical radiation received by the detector 112 along the optical axis 124. Instead of one physical nozzle 108' there may be a plurality of similar nozzles and/or sub-nozzles as shown in FIGS. 2A and 2B.

In an embodiment, the jet 114, 114' may circulate the fluidal matter 100 in the measurement chamber 106. That is, the jet 114, 114' may make the fluidal matter 100 move in the measurement chamber 106. In this manner, the circulated fluidal matter 100 may also be homogenized.

In an embodiment, the jet 114, 114' may dilute the fluidal matter 100 with the flowable matter 110 in the measurement chamber 106. When the jet 114, 114', which doesn't have particles 104, is emitted and mixed in the fluidal matter 100, the consistency of the fluidal matter 100 may decrease.

In an embodiment an example of which is illustrated in FIGS. 1A and 3, the apparatus may comprise a pump arrangement 150 may pump the flowable matter 110 to the at least one nozzle 108, 108'. The pump arrangement 150 may be a part of the apparatus in all Figures and embodiments. The pump arrangement 150 may comprise one pump which pumps the flowable matter 110 to all nozzles 108, 108' or each nozzle 108, 108' may have its own pump, i.e. the pump may be nozzle-specific. One pump of the pump arrangement 150 may pump the flowable matter to more than one nozzle 108, 108'. The data processing unit 116 may control the operation of the pump arrangement 150. A pressure of the flowable matter 110 in the nozzle 108, 108' may be generated with a pool of the flowable matter 110 which is in a higher location than the nozzle 1108, 108' such that the flowable matter 110 is allowed to flow from the pool to the nozzle 108, 108'. However, the pool may need to be filled with the flowable matter 110 using the pump arrangement 150.

Figure 4:
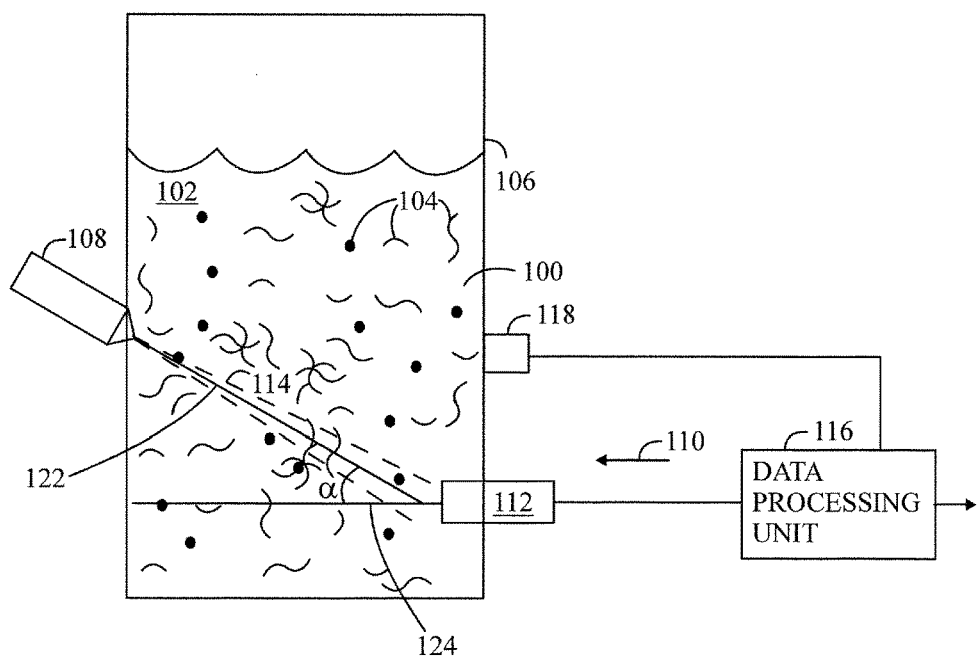
FIG. 4 illustrates an example of an apparatus for optically measuring fluidal matter, the apparatus being configured to direct a jet at an oblique angle with respect to an optical axis of the detector.

FIG. 4 illustrates an example of an embodiment, where the jet 114 is directed towards the optical detector 112 at an oblique angle α with respect to the optical axis 124. The oblique angle α may vary in the range from 0° to 180°, not including the limits, i.e.]0°, 180° [.

In an embodiment, the pump arrangement 150 may pulsate the jet 114, 114' of the flowable matter 110 from the at least one nozzle 108, 108'. The data processing unit 116 may control the operation of the pump arrangement 150 for causing the pulsation. The pulsation may vary intensity of pressure of the jet 114, 114' in a determined or random manner. That is, the pressure within the nozzle 108, 108' may be increased or decreased periodically by the pump arrangement 150 or by some other means. The pressure in the nozzle 108, 108' and the speed of the jet 114, 114' may be made to vary according to a square wave, triangle wave or a sine wave, for example.

In an embodiment, the pump arrangement 150 may suck the fluidal matter 100 from the measurement chamber 106 and pump the fluidal matter 110 to the at least one nozzle 108, 108' which may then emit the jet 114, 114' the fluidal matter 100 into the measurement chamber 106. In this embodiment, the fluidal matter 100 may be used as the flowable matter 110. If the fluidal matter 100 as such is circulated in this manner, the consistency of the fluidal matter may be kept unchanged. In an embodiment, at least a part of the particles 104 is removed by filtering before emitting the fluidal matter 100 back to the measurement chamber 106. Then the consistency of the fluidal matter 100 in the measurement chamber 106 may decrease because the relative amount of the medium may increase.

In an embodiment, the apparatus may optically measure at least one of the following properties of the fluidal matter 100, which may be paper stock, in the measurement chamber 106: kappa number, brightness. Other measurements may be a particle size measurement and a spectral measurement, for example, which are suitable for sewage and mineral processes in addition to the pulp process.

Figure 5:
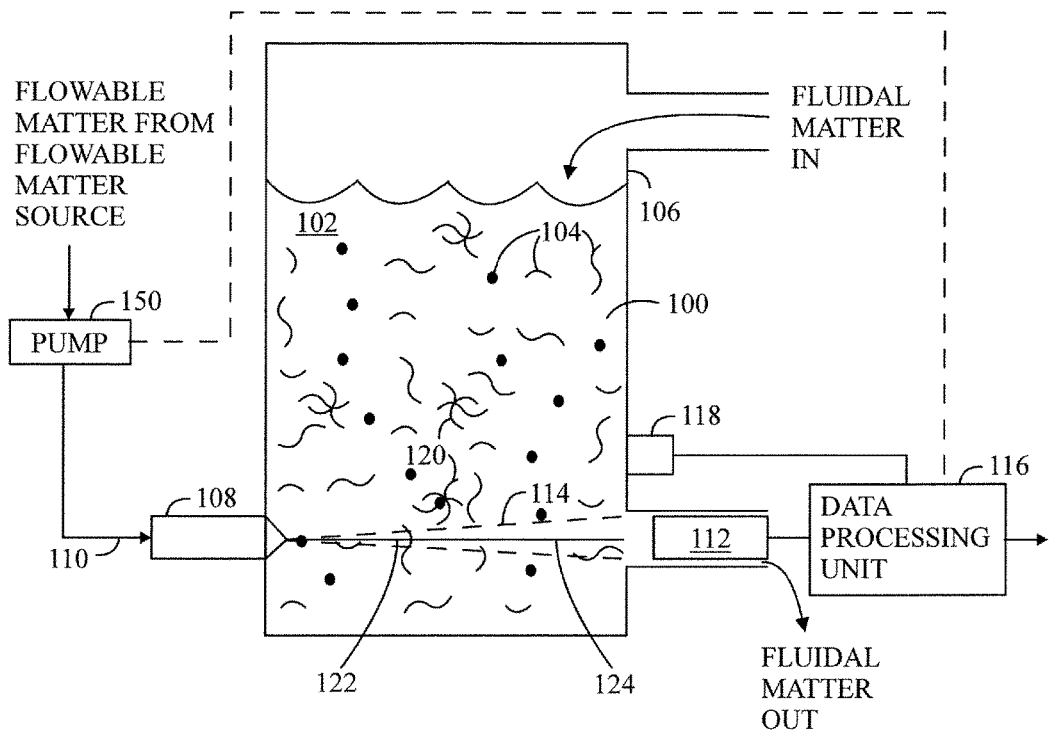
FIG. 5 illustrates an example of an apparatus for optically measuring fluidal matter, a measurement chamber being a flow-through chamber.

FIG. 5 illustrates an example of an embodiment, where the fluidal matter 100 may flow through the measurement chamber 106. The measurement chamber 106 may be a main process pipe or the measurement chamber 106 may be a part of the sample pipe to which a sample of the fluidal matter 100 is taken from the main process pipe. The fluidal matter 100 may enter the measurement chamber 106 at the upper part of the measurement chamber 106 (may also enter at the lower part). The fluidal matter 100 may then flow out of the measurement chamber 106 at the lower part. A potential location for an exit of the fluidal matter 100 is at or in adjacency of the optical detector 112. The fluidal matter 100 may flow through the measurement chamber 106 also in other embodiments than that of FIG. 5.

Figure 6:
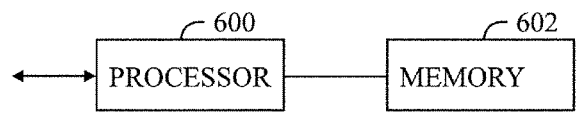
FIG. 6 illustrates an example of a signal processing unit with at least one processor and at least one memory.

In an embodiment an example of which is illustrated in FIG. 6, the signal processing unit 116 may comprise one or more processors 600 and one or more memories 602 including a computer program code. The one or more memories 602 and the computer program code may, with the one or more processors 600, allow the signal processing unit 152 to control the operation of the apparatus.

Figure 7:
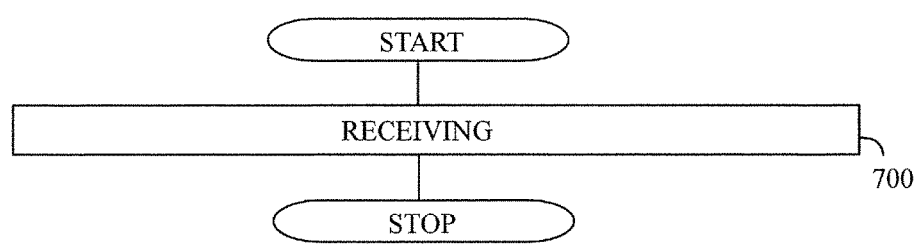
FIG. 7 illustrates of an example of a flow chart of a method for optically measuring fluidal matter having fluid as medium and particles non-dissolved in the medium.

FIG. 7 is a flow chart of the method for optically measuring fluidal matter 100 having fluid as medium 102 and particles 104 non-dissolved in the medium 102. In step 700, flowable matter is received, and a jet 114, 114' of the flowable matter 100 is emitted, by at least one nozzle 108, 108', towards or fromwards an optical detector 112, which is associated with a measurement chamber 106, which has the fluidal matter 100, and which receives optical radiation from the fluidal matter 100 in the measurement chamber 106.

The method pulsation may be implemented as a logic circuit solution or computer program. The computer program may be placed on a computer program distribution means for the distribution thereof. The computer program distribution means is readable by a data processing device, and it encodes the computer program commands, carries out the measurements and optionally controls the processes on the basis of the measurements.

The computer program may be distributed using a distribution medium which may be any medium readable by the controller. The medium may be a program storage medium, a memory, a software distribution package, or a compressed software package. In some cases, the distribution may be performed using at least one of the following: a near field communication signal, a short distance signal, and a telecommunications signal.

It will be obvious to a person skilled in the art that, as technology advances, the inventive concept can be implemented in various ways. The invention and its embodiments are not limited to the example embodiments described above but may vary within the scope of the claims.

The invention claimed is:

1. An apparatus for optically measuring fluidal matter having fluid as medium and particles non-dissolved in the medium wherein the apparatus comprises a measurement chamber, which is configured to contain the fluidal matter, and at least one nozzle;

the at least one nozzle is configured to receive flowable matter and emit a jet of the flowable matter, which is configured to break aggregates of the particles of the fluidal matter, towards or fromwards an optical detector which is associated with the measurement chamber and configured to receive optical radiation from the fluidal matter in the measurement chamber.

2. The apparatus of claim 1, wherein at least one of the at least one nozzle is configured to emit its jet of the flowable matter such that the longitudinal axis of each of the jet and an optical axis of the optical detector are co-axial.

3. The apparatus of claim 1, wherein a direction of flow of a jet from the at least one nozzle along the longitudinal axis of the jet is co-directional with a reception direction of the optical radiation of the optical detector.

4. The apparatus of claim 1, wherein a direction of flow of a jet from the at least one nozzle along the longitudinal axis of the jet is opposite-directional to a reception direction of the optical radiation received by the optical detector along the optical axis.

5. The apparatus of claim 1, wherein the jet is configured to circulate the fluidal matter in the measurement chamber.

6. The apparatus of claim 1, wherein the jet is configured to dilute the fluidal matter with the flowable matter in the measurement chamber.

7. The apparatus of claim 1, wherein the apparatus comprises a pump arrangement configured to pump the flowable matter to the at least one nozzle.

8. The apparatus of claim 7, wherein the pump arrangement is configured to pulsate the jet of the flowable matter from the at least one nozzle.

9. The apparatus of claim 8, wherein the pump arrangement is configured to suck the fluidal matter from the measurement chamber and emit the jet of the fluidal matter to the measurement chamber.

10. The apparatus of claim 1, wherein the apparatus is configured to optically measure at least one of the following properties of the fluidal matter, which is paper stock in the measurement chamber: kappa number, brightness.

11. A method for optically measuring fluidal matter having fluid as medium and particles non-dissolved in the medium, the method comprising receiving flowable matter and emitting, by at least one nozzle, a jet of the flowable matter, which breaks aggregates of the particles of the fluidal matter, towards or fromwards an optical detector, which is associated with a measurement chamber, which has the fluidal matter and which receives optical radiation from the fluidal matter in the measurement chamber.

\* \* \* \* \*